United States Patent [19]

Fukui et al.

[11] Patent Number: 5,560,965

[45] Date of Patent: Oct. 1, 1996

[54] DRY FLOWER AND PROCESS FOR PRODUCTION OF SAME

[75] Inventors: Hiroshi Fukui; Michihiro Yamaguchi, both of Yokohama; Naoto Okamoto; Yasushi Nishimura, both of Osaka, all of Japan

[73] Assignee: Shiseido Company, Ltd., Tokyo, Japan

[21] Appl. No.: 594,386

[22] Filed: Jan. 31, 1996

Related U.S. Application Data

[63] Continuation of Ser. No. 284,627, filed as PCT/JP93/01817 on Dec. 15, 1993 published as WO94/1317 on Jun. 23, 1994, abandoned.

[30] Foreign Application Priority Data

Dec. 16, 1992 [JP] Japan ................................. 4-354523
Mar. 30, 1993 [JP] Japan ................................. 5-095323

[51] Int. Cl.$^6$ ..................................................... A01N 3/00
[52] U.S. Cl. ............................ 428/24; 427/4; 427/255.6; 428/22
[58] Field of Search ........................... 427/4, 255.6, 421, 427/387; 428/22, 24

[56] References Cited

U.S. PATENT DOCUMENTS

| | | | |
|---|---|---|---|
| 4,198,441 | 4/1980 | Young et al. ................................. | 427/4 |
| 4,225,647 | 9/1980 | Parent ........................................... | 427/226 |
| 4,349,459 | 9/1982 | Romero-Sierra et al. .................... | 427/4 |
| 4,783,351 | 11/1988 | Baker ............................................ | 427/4 |
| 5,073,195 | 12/1991 | Cuthbert et al. ............................. | 428/22 |
| 5,227,205 | 7/1993 | Dubrow et al. .............................. | 428/24 |

FOREIGN PATENT DOCUMENTS

| | | |
|---|---|---|
| 2020360 | 1/1992 | Canada . |
| 0279108 | 8/1988 | European Pat. Off. . |
| 52-3587 | 1/1977 | Japan . |
| 54-135078 | 10/1979 | Japan . |
| 55-9652 | 1/1980 | Japan . |
| 5842682 | 1/1980 | Japan . |
| 59-44301 | 3/1984 | Japan . |
| 59-227801 | 12/1984 | Japan . |
| 60-101162 | 6/1985 | Japan . |
| 62-265202 | 11/1987 | Japan . |
| 63-92687 | 4/1988 | Japan . |
| 63-99285 | 4/1988 | Japan . |

OTHER PUBLICATIONS

Derwent Abstract 47910 of JA 0135078, Nizu, Oct. 1979.
Database WPI, Derwent Publications Ltd., Week 9207, JP-A-3 294 202, Dec. 25, 1991.
Database WPI, Derwent Publications Ltd., Week 7904, JP-A-53 141 741, Dec. 9, 1978.
Patent Abstracts of Japan, vol. 15, No. 80, JP-A-23 004 002, Feb. 1991.
Database WPI, Derwent Publications Ltd., Week 9402, JP-A-5 319 862, Dec. 1993.
Patent Abstracts of Japan, vol. 12, No. 202, JP-A-63 005 001, Jun. 1988.
Patent Abstracts of Japan, vol. 16, No. 470, JP-A-41 069 501, Jun. 1992.

*Primary Examiner*—Diana Dudash
*Attorney, Agent, or Firm*—Foley & Lardner

[57] ABSTRACT

A dry flower, and a process for producing the same, coated on its surface with a polymer film of $(R^1HSiO)_a(R^2R^3SiO)_b(R^4R^5R^6SiO_{1/2})_c$ or (2) a film of one or more polymers selected from (i) photopolymerizable polymers, (ii) silane coupling agent polymers, and (iii) copolymers of photopolymerizable monomers and silane coupling agents.

7 Claims, No Drawings

DRY FLOWER AND PROCESS FOR PRODUCTION OF SAME

This application is a continuation of application Ser. No. 08/284,627, filed as PCT/JP93/01817 on Dec. 15, 1993, published as WO94/13137 on Jun. 23, 1994, now abandoned.

TECHNICAL FIELD

The present invention relates to a dry flower coated on its surface with a silicone polymer film and to a process for producing the same.

The term "dry flower" used herein means a dried flower, stem, and leaf. Note that, here, "dried" includes in addition to just removal of moisture by evaporation the substantive removal of moisture by substitution of moisture with another organic compound etc.

The dry flower according to the present invention is water repellent, so is resistant to absorption of moisture even under humid conditions and therefore can be kept from discoloring or molding due to the inclusion of moisture and, as a result, will not change in the color or the shape of its flower, leaf (or leaves) and stem even under severe conditions.

BACKGROUND ART

The conventional process for the production of a dry flower has been to dry a fresh flower with a silica gel. To boost the efficiency of this, various salts have been added and various sources of heat used so as to raise the uniformity of the drying.

A conventional dry flower, however, absorbs moisture when placed under relatively high humidity conditions, and therefore, quickly discolors or molds and changes from its original appearance. To prevent this, it may be considered to provide a coating of a water repellent polymer, but if a flower is immersed in a polymer solution, the polymer will cover the surface of the flower thickly and the original form cannot be maintained.

On the other hand, for the purpose of maintaining the color and shape of a cut flower and dry flower, it has been proposed to coat the surfaces with an adhesive (Japanese Unexamined Patent Publication (Kokai) No. 59-44301, Japanese Unexamined Patent Publication (Kokai) No. 59-227801) or a viscous agent (Japanese Unexamined Patent Publication (Kokai) No. 62-265202). In each case, however, the treatment solution is applied to the object to be treated by brushing, spraying, immersion, etc. The surface of the flower is heavily coated with the adhesive or viscous agent, so there is the disadvantage that the original natural appearance cannot actually be maintained.

DISCLOSURE OF THE INVENTION

Accordingly, the present invention is to solve the above-mentioned problems in the prior art and to provide a dry flower, and a process for producing the same, which gives improved water repellency, stability of color and shape, etc. while maintaining the natural appearance and other original desirable characteristics of the dry flower.

In accordance with the present invention, the above-mentioned object can be achieved by coating the surface of the dry flower with a thin, transparent polymer film which can impart sufficient water repellency and further does not detract from the original natural appearance.

According to the first aspect of the present invention, there is provided a dry flower coated on its surface with a silicone polymer film by bringing at least one silicone compound of the formula (I):

$$(R^1HSiO)_a(R^2R^3SiO)_b(R^4R^5R^6SiO_{1/2})_c \qquad (I)$$

wherein $R^1$, $R^2$, $R^3$ and independently represent a hydrogen atom or a $C_1$ to $C_{10}$ hydrocarbon group, preferably a $C_1$ to $C_4$ hydrocarbon group (in particular an alkyl group) or aryl group (for example, phenyl group), which may be substituted with at least one halogen atom, provided that $R^1$, $R^2$, and $R^3$ are not simultaneously hydrogen atoms, and $R^4$, $R^5$, and $R^6$ independently represent a hydrogen atom or a $C_1$ to $C_{10}$ hydrocarbon group, preferably a $C_1$ to $C_4$ hydrocarbon group (in particular an alkyl group) or aryl group (for example, phenyl group), which may be substituted with at least one halogen atom, a is 0 or an integer of 1 or more, b is 0 or an integer of 1 or more, and c is 0 or 2, the sum of a and b being an integer of 3 or more when c is 0, into contact with a dried flower etc. (dry flower) in the form of a vapor and allowing the silicone compound to be polymerized on the surface of the dry flower.

According to the second aspect of the present invention, the dry flower coated with the above-mentioned polymer film may be obtained by bringing (i) a photopolymerization initiator and photopolymerizable monomer and/or (ii) a silane coupling agent into contact with a surface of a dry flower in the vapor phase state and causing the polymerization on the surface of the dry flower. Alternatively, before, after, or simultaneous with this step, by bringing at least one silicone compound having a hydrosilyl bond (Si—H) into contact with the surface of the dry flower in a vapor phase state and causing it to polymerize on the surface of the dry flower, a dry flower coated on its surface with a polymerized silicone compound film is obtained, whereby the stability etc. can be further improved.

BEST MODE FOR CARRYING OUT THE INVENTION

The present invention will now be explained in further detail below.

As explained already, when it has been attempted to coat a dry flower with a polymer (for example, a vinyl acetate based resin disclosed in Japanese Unexamined Patent Publication (Kokai) No. 59-44301 or a polyvinyl alcohol disclosed in Japanese Unexamined Patent Publication (Kokai) No. 62-265202), with the method of immersion in the polymer itself or a solution of the polymer in an organic solvent or of spraying of the same on the flower and then drying, the polymer has been coated thickly and nonuniformly, and therefore, the original delicate appearance of the dry flower ends up being changed.

In the first aspect of the present invention, by bringing a gaseous silicone compound into contact with a dry flower, the flower is coated with an extremely thin film without being changed in its shape and the dry flower is given water repellency to improve its stability.

In the present invention, the contact between the vapor state silicone compound having the above-mentioned formula (I) and the dry flower is performed under a temperature of not more than 120° C., preferably room temperature to 100° C., and under a pressure of preferably not more than 200 mmHg, more preferably not more than 100 mmHg, in a sealed container, so as to enable the vapor of the silicone compound having the above-mentioned formula (I) to deposit on the surface of the dry flower in a molecular state. Alternatively, the contact between the vapor state silicone compound having the formula (I) and the dry flower is performed by supplying a mixed gas of the silicone compound having the formula (I) and a carrier gas to a powder under a temperature of not more than 120° C., preferably room temperature to 100° C.

The silicone compound having the above-mentioned formula (I) comprises two groups. The first group corresponds to the case wherein c=0 in the formula (I) and is a cyclic silicone compound having the general formula (II):

wherein, $R^1$, $R^2$, $R^3$, a, and b are as defined above, preferably $R^1$, $R^2$, and $R^3$ are, independently, a $C_1$ to $C_4$ lower alkyl group or aryl group (e.g., phenyl group), which may be substituted with at least one halogen atom and the sum of a and b is from 3 to 7). Typical examples of the compound are as follows:

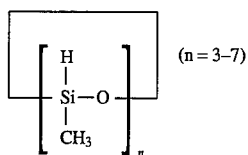
(III)

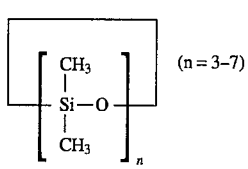
(IV)

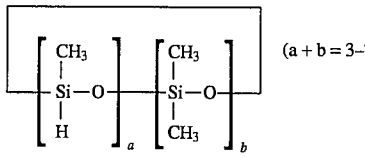
(V)

The above-mentioned compounds (III), (IV), and (V) may be used alone or in any mixtures thereof.

In the above formulae, n (or a+b) is preferably 3 to 7. The smaller the value of n, the lower the boiling point, so the greater the amount which evaporates and is adsorbed on the dry flower. In particular, a trimer and tetramer easily polymerize due to their steric properties, and therefore, are particularly suitable. Further, the silicone compound having a hydrogen atom therein has a high reactivity, and therefore, is suitable for the surface treatment.

As examples of the cyclic silicone compounds of the formula (I), there may be mentioned dihydrogenhexamethylcyclotetrasiloxane, trihydrogenpentamethylcyclotetrasiloxane, tetrahydrogentetramethylcyclotetrasiloxane, dihydrogenoctamethylcyclopentasiloxane, trihydrogenheptamethylcyclopentasiloxane, tetrahydrogenhexamethylcyclopentasiloxane, and pentahydrogenpentamethylcyclopentasiloxane.

The second group of the silicone compounds having the above-mentioned formula (I) corresponds to the case wherein c=2 in the formula (I) and the general formula (VI):

wherein $R^1$, $R^2$, $R^3$, $R^4$, $R^5$, $R^6$, a, and b are as defined above and c is 2, preferably $R^1$ to $R^6$ are, independently, a $C_1$ to $C_4$ lower alkyl group or aryl group (e.g., phenyl group) which may be substituted with at least one halogen atom, and the sum of a and b is 2 to 5. As typical examples of the compounds, there may be mentioned compounds having the general formula (VII):

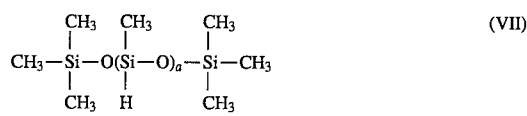

wherein a is 2 to 5.

As examples of the straight chain silicone compounds of the formula (III), there may be mentioned 1,1,1,3,5,7,7,7-octamethyltetrasiloxane, 1,1,1,3,5,7,9,9,9-nonamethylpentasiloxane, and 1,1,1,3,5,7,9,11,11,11-decamethylhexasiloxane.

There are two types of structures of the silicone polymer films coated on the surface of the dry flower. That is, when the polymerization is caused by a siloxane bond (—Si—O—Si—), the resultant silicone polymer has a straight chain structure including a —Si—O—Si— unit. On the other hand, when the polymerization is caused by a dehydrogenation reaction of the hydrosilyl bond (Si—H) in the presence of a small amount or trace amount of $H_2O$ or $O_2$, the following polymerization of the Si—H portion occurs:

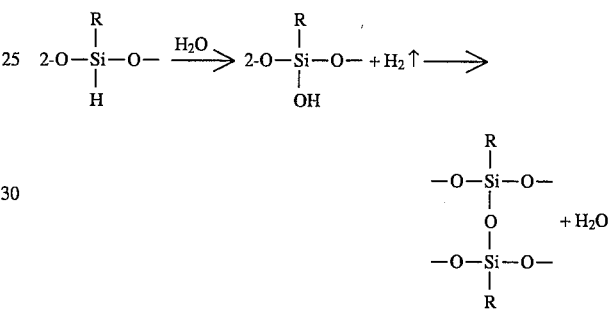

and gives a network structure having units of the general formula (VIII) contained in the silicone polymer.

(VIII)

A preferably network polymer is one in which the $R^1HSiO$ units are converted to $R^1SiO_{3/2}$ units for at least 20% of all the Si atoms.

The amount of the silicone compound of the formula (I) which is added (amount of treatment) is not particularly determined. A desired amount is determined in consideration of supplying the amount of silicone compound necessary and sufficient for coating substantially the entire surface of the dry flower.

That is, the present invention does not determine, in advance, the amount of addition of the treating agent. The treatment is performed so that the necessary and sufficient amount of the treating agent is supplied and the endpoint is naturally led to. Therefore, the amount of addition or the amount of the deposited polymer coating differ according to the type of the dry flower used. In general, the amount is 0.0005 to 10% by weight of the total weight of the dry flower.

Thus, in the present invention, any type of dry flower can be treated without excess or insufficiency. This is because the method of addition of the treating agent differs from that of the past.

According to the basic embodiment of the first aspect of the present invention, the dry flower and the silicone compound (for example, cyclic organosiloxane) may be placed in separate containers with their tops left open in a sealed chamber (for example of not more than 100° C.).

The present invention does not require any special apparatus since it is based on the above-mentioned simple principle. For example, any sealed chamber (for example, a sealed chamber held at a constant temperature), for example, a desiccator or thermostatic chamber, may be used. Further, it is possible to use a desiccator for small amounts of treatment. Ideally, however, an apparatus which can be deaerated after the treatment is desirable and use of a gas sterilizer is preferred.

According to another embodiment of the first aspect of the present invention, it is possible to place just the dry flower, in advance, into a sealed chamber of not more than 120° C., preferably not more than 100° C., cause vaporization of the silicone compound at a predetermined partial pressure in another sealed chamber of not more than 120° C., and introduce the silicone compound vapor into the chamber, where the dry flower has been placed, by a pipe etc. The pressure of the above-mentioned system is not particularly limited, but the polymerization is preferably performed at not more than 200 mmHg, preferably no more than 100 mmHg. In both embodiments, the treatment time is from 30 minutes to 150 hours. The unpolymerized silicone compound is then removed by degassing to obtain the desired product.

According to a further embodiment of the first aspect of the present invention, it is possible to treat the dry flower by bringing it into contact with a silicone compound having the formula (II) in the form of a mixed gas with a carrier gas (for example, by supplying the compound to the surface of the dry flower). The mixing of the silicone compound having the formula (II) and the carrier gas may be performed by heating the silicone compound having the formula (II) when necessary until the vapor pressure of the silicone compound becomes not less than 1 mmHg, preferably not less than 10 mmHg, then introducing a stream of a carrier gas into the silicone compound having the formula (II) or on the surface of the silicone compound. The speed of supply of stream of carrier gas may be suitably determined, for example, by the vapor pressure of the silicone compound having the formula (II), the type and amount of the dry flower, and the volume of the treatment container. It is preferable to adjust things so that the treatment can be performed in 30 minutes to 150 hours.

As the carrier gas, an inert gas, for example, nitrogen, argon, or helium, is preferable.

Next, in the second aspect of the present invention, it is possible to coat a dry flower with an extremely thin film, without changing its color or shape, and give it water repellency and improved stability by bringing a photopolymerization initiator and a photopolymerizable monomer, a silane coupling agent, or both or, further, these and a silicone compound having a hydrosilyl bond (Si—H) into contact with the dry flower in a vapor phase state (gaseous state) and causing polymerization of the same.

The term "photopolymerization initiator" used herein means light absorbing molecules which produce radicals upon irradiation by ultraviolet ray energy and initiate a radical reaction. Specifically, mention may be made of benzoin isobutyl ether, 1-(4-isopropylphenyl)-2-hydroxy-2-methylpropane-1-on, diethoxy acetophenone, etc.

The photopolymerizable monomer means a monomer having unsaturated double bonds (acryloyl group, methacryloyl group, allyl group, vinyl group, and the other vinyl functional groups) which polymerizes under irradiation by ultraviolet light in the presence of the photopolymerization initiator. More specifically, there may be mentioned 2,2,2-trifluoroethyl acrylate, ethylene glycol dimethacrylate, stearyl acrylate, glycidyl methacrylate, tetrahydrofurfuryl acrylate, allyl methacrylate, etc. In the present invention, the vapor phase polymerizable oligomers derived from these monomers are also treated as photopolymerizable monomers.

The silane coupling agent is an organic silicon compound having in the same molecule an organic functional group (acryloyl group, methacryloyl group, alkyl group, fluoroalkyl group, amino group, epoxy group, etc.) and a hydrolyzable group (alkoxyl group, silano group), such as 3-methacryloxypropyltrimethoxysilane, 3,3,3-trifluoropropyltrimethoxysilane, aminopropyltrimethoxysilane, etc. In the present invention, use may be made even of ones in which the sites corresponding to the organic functional group are alkyl groups or other groups having a relative low reactivity, and therefore, these compounds are included in the definition of silane coupling agents.

Note that, when a silane coupling agent is used, the polymerization reaction progresses if there is even a slight amount of moisture present by adjustment of the temperature conditions, but when use is made of a photopolymerization initiator and photopolymerizable monomer, the polymerization is performed by bringing the same into contact with the surface of the dry flower in the vapor phase state and then irradiating ultraviolet light.

The silicone compounds having the hydrosilyl bonds (Si—H) used in the present invention are not particularly limited so long as vapor phase polymerization is possible at a relatively low temperature (preferably not more than 120° C.). As such silicone compounds, use may be made of the compounds having the formula (I), among which dihydrogen-hexamethylcyclotetrasiloxane, trihydrogenpentamethyl-cyclotetrasiloxane, tetrahydrogentetramethylcyclo-tetrasiloxane, dihydrogenoctamethylcyclopentasiloxane, trihydrogenheptamethylcyclopentasiloxane, tetrahydrogenhexamethylcyclopentasiloxane, pentahydrogenpentamethyl-cyclopentasiloxane, and other cyclic silicones are preferred.

When bringing at least one silicone compound having the hydrosilyl bond into contact with the surface of a dry flower in the vapor phase state and causing polymerization on the surface of the dry flower, the main polymer film itself may be copolymerized with the silicone compound or the polymerized silicone compound film layer may be formed on the inside or outside of the main polymer film layer. In either case, the stability of the dry flower is improved.

Note that a plurality of the polymerized silicone compound films may be provided, for example, they may be provided at both of the inside and outside of the main polymer film, and that the polymerized silicone compound film layers may be partially chemically bonded to the polymer film layer.

In the present invention, the contact between the vapor phase state photopolymerizable monomer etc. and dry flower may be performed in a sealed container under temperature conditions of not more than 120° C., preferably not more than 100° C., to cause deposition of the above-mentioned components on the surface of the dry flower in a molecular state. At this time, when contact is performed under a reduced pressure, the speed of diffusion of the monomer etc. becomes faster, and therefore, more efficient treatment is possible. In the case of a photopolymerizable monomer, polymerization is caused after the deposition by the irradiation of ultraviolet light.

Further, the contact may be performed by placing the dry flower in a sealed container and supplying into the sealed container a mixed gas of the vapor of the photopolymerizable monomer etc. and a carrier gas under a temperature of not more than 120° C., preferably not more than 100° C. In the case of a photopolymerizable monomer, polymerization is caused after the deposition by the irradiation of ultraviolet light.

Further, by performing the same or similar processing using a silicone compound having a hydrosilyl bond (Si—H) before, after, or simultaneous with the above processing, it is possible to obtain a superior water repellency and give further stability to the dry flower.

According to the basic embodiment of the second aspect of the present invention, the dry flower and the (i) photopolymerization initiator and photopolymerizable monomer or (ii) silane coupling agent or (iii) the two of them may be placed in separate containers with their tops left open in a sealed chamber (for example of not more than 100° C.). In the case of a photopolymerizable monomer, ultraviolet light is then irradiated for causing the polymerization.

Further, the same type of treatment may be performed for silicone compounds having hydrosilyl bonds as well.

The present invention does not require any special apparatus since it is based on the above-mentioned simple principle. For example, any sealed chamber (for example, a sealed chamber capable of being held at a constant temperature), for example, a desiccator or thermostatic chamber, may be used. Further, it is possible to use a desiccator for small amounts of treatment. Ideally, however, an apparatus which can be deaerated after the treatment is desirable.

According to another embodiment of the second aspect of the present invention, it is possible to place just the dry flower, in advance, into a sealed chamber of not more than 120° C., preferably not more than 100° C., cause vaporization of the photopolymerization initiator and photopolymerizable monomer, the silane coupling agent, or the two of these at a predetermined partial pressure in another sealed chamber of not more than 120° C., and introduce the vapor into the chamber where the dry flower has been placed (for example, by a pipe). In the case of a photopolymerizable monomer, ultraviolet light is then irradiated for causing the polymerization. Further, the same or similar treatment may be performed for silicone compounds having hydrosilyl bonds as well.

The pressure of the above-mentioned system is not particularly limited, but under reduced pressure, the diffusion rate of the monomer etc. becomes higher, and therefore, the efficient treatment becomes possible.

In both embodiments, the treatment time is from 30 minutes to 150 hours. The unpolymerized photopolymerization initiator, photopolymerizable monomer, silane coupling agent, etc. are then removed by degassing to obtain the desired product.

According to another embodiment of the second aspect of the present invention, it is possible to bring into contact with the surface of the dry flower the photopolymerization initiator and photopolymerizable monomer, the silane coupling agent, etc. in the form of a mixture with a carrier gas. In the case of a photopolymerizable monomer, polymerization is subsequently caused by irradiating ultraviolet light. Further, the same treatment may be applied in the case of a silicone compound having a hydrosilyl bond.

The mixing of the photopolymerization initiator and photopolymerizable monomer, the silane coupling agent, or the two of these with the carrier gas may be performed by heating when necessary until the vapor pressure of the former becomes not less than 1 mmHg, preferably not less than 10 mmHg, then introducing a stream of a carrier gas. The speed of supply of stream of carrier gas may be suitably determined, for example, by the vapor pressure of the photopolymerizable monomer etc., the type and amount of the dry flower, and the volume of the treatment container. It is preferable to adjust things so that the treatment can be performed in 30 minutes to 150 hours.

As the carrier gas, an inert gas, for example, nitrogen, argon, helium, etc., is preferable, but depending on the conditions, use may also be made of air or a mixed gas containing the above-mentioned inert gas, in which is mixed in a gaseous molecular state, water vapor.

EXAMPLES

The present invention will now be further illustrated by, but is by no means limited to, the following Examples.

Example 1

A red rose dried by silica gel and 10 g of tetramethylcyclotetrasiloxane were placed in a vacuum desiccator. This was evacuated by an aspirator for 3 minutes, then the cock closed.

This was allowed to stand at room temperature for 24 hours, then air was introduced into the vacuum desiccator to return the pressure to ordinary pressure and then the rose was taken out.

The surface treated red rose did not show any change in color or shape from before the treatment, but exhibited a remarkable water repellency.

The surface treated red rose of Example 1 and a non-surface-treated dried red rose were placed in 500 ml polypropylene cups, together with absorbent wadding containing water. The tops of the cups were covered with Saran wrap (a polyvinylidene chloride wrapping film) to seal them and these were allowed to stand at room temperature for one day.

The untreated dried red rose lost color, but the surface treated red rose maintained its red color, and therefore, the surface treatment was observed to be effective.

Example 2

A gentian dried by silica gel was placed in a 10 liter dryer (made of stainless steel, with insulating jacket).

On the other hand, 100 g of 1,3,5-tris(3,3,3-trifluoropropyl)-1,3,5-trimethylcyclotrisiloxane was placed in a reaction solution feeder tank connected to the dryer by a stainless steel pipe. This was introduced into the dryer by bubbling nitrogen from the bottom of the reaction solution feeder tank (500 ml/min). The temperature was 50° C. in the reaction solution feeder tank and room temperature in the dryer.

After 4 hours of the reaction, the supply of the reaction solution was stopped and just nitrogen was introduced into the dryer. After 2 hours, the surface-treated gentian was removed.

The surface treated gentian exhibited a remarkable water repellency in the same way as in Example 1 and did not change in color or shape from before the treatment.

The surface treated gentian of Example 2 and a non-surface-treated dried gentian were allowed to stand, together with absorbent wadding containing water, at 37° C. for 1 week, whereupon the untreated gentian was observed to have black mold, while no mold was observed on the surface-treated gentian.

In the above way, a dry flower having water repellency was obtained by the present invention. In particular, the color stability and mold resistance were improved in systems in the copresence of moisture.

Example 3

A red rose dried by silica gel, 20 g of 2,2,2-trifluoroethyl acrylate, and 1 g of benzoin isobutyl ether were placed in a vacuum desiccator. This was evacuated by an aspirator for 3 minutes, then the cock closed.

These were allowed to stand at room temperature for 24 hours, then air was introduced into the vacuum desiccator to return the pressure to ordinary pressure and then the rose was taken out.

Next, the dry flower was irradiated with ultraviolet light for 3 minutes to form a coating film.

The surface treated red rose did not show any change in color or shape from before the treatment, but exhibited a remarkable water repellency.

The surface treated red rose of Example 3 and an un-surface-treated dried red rose were placed in 500 ml polypropylene cups together with dishes containing water. The tops of the cups were covered with polyvinylidene chloride film (Saran wrap: made by Asahi Chemical Industry Co., Ltd.) and these were allowed to stand at room temperature for 10 days.

The untreated dried red rose discolored and turned brown and was observed to have white and black mold, but the surface treated red rose maintained its red color and was not observed to have any mold, and therefore, the surface treatment was observed to be effective.

Example 4

A red rose dried by silica gel and 10 g of 3,3,3-trifluoropropyltrimethoxysilane were placed in a vacuum desiccator. This was evacuated by an aspirator for 3 minutes, then the cock closed.

This was allowed to stand at room temperature for 6 hours, then air was introduced into the vacuum desiccator to return the pressure to ordinary pressure and then the rose was taken out.

The surface treated red rose did not show any change in color or shape from before the treatment, but exhibited a remarkable water repellency.

The surface treated red rose of Example 4 and an un-surface-treated dried red rose were placed in 500 ml polypropylene cups, together with dishes of water. The tops of the cups were covered with Saran wrap to seal them and these were allowed to stand at room temperature for 10 day.

The untreated dried red rose discolored and turned brown and was observed to have white and black mold, but the surface treated red rose maintained its red color and was not observed to have any mold, and therefore, the surface treatment was observed to be effective.

Example 5

A yellow rose dried by silica gel, 20 g of ethylene glycol dimethacrylate, and 1 g of benzoin isobutyl ether were placed in a vacuum desiccator. This was evacuated by an aspirator for 3 minutes, then the cock closed.

This was allowed to stand at 80° C. for 24 hours, then air was introduced into the vacuum desiccator to return the pressure to ordinary pressure and then the rose was taken out.

Next, the dry flower was irradiated with ultraviolet light for 3 minutes to form a coating.

Then, the flower and 10 g of 1,3,5,7-tetramethylcyclotetrasiloxane were placed in a vacuum desiccator which was then evacuated by an aspirator for 3 minutes and then the cock closed.

This was allowed to stand at room temperature for 15 hours, then air was introduced into the vacuum desiccator to return the pressure to ordinary pressure and then the rose was taken out.

The surface treated yellow rose did not show any change in color or shape from before the treatment, but exhibited a remarkable water repellency.

The surface treated yellow rose of Example 5 and an un-surface-treated dried yellow rose were placed in 500 ml polypropylene cups together with dishes containing water. The tops of the cups were covered with Saran wrap and these were allowed to stand at room temperature for 15 days.

The untreated dried yellow rose discolored and turned brown and was observed to have white and black mold, but the surface treated yellow rose maintained its yellow color and was not observed to have any mold, and therefore, the surface treatment was observed to be effective.

Example 6

A gentian dried by silica gel was placed in a 10 liter dryer (made of stainless steel, with insulating jacket).

On the other hand, 50 g of 3-methacryloxypropyltrimethoxysilane, 50 g of stearyl acrylate, and 5 g of 1-(4-isopropylphenyl)-2-hydroxy-2-methylpropane-1-one were placed in a reaction solution feeder tank connected to the dryer by a stainless steel pipe. These were introduced into the dryer by bubbling nitrogen from the bottom of the reaction solution feeder tank (500 ml/min). The temperature was 50° C. in the reaction solution feeder tank and the dryer.

After 4 hours of reaction, the supply of the reaction solution was stopped and just nitrogen was introduced into the dryer. After 2 hours, the surface-treated gentian was removed.

Next, the dry flower was irradiated with ultraviolet light for 3 minutes to form a coating film.

The surface treated gentian exhibited a remarkable water repellency and did not change in color or shape from before the treatment.

The surface treated gentian of Example 6 and an un-surface-treated dried gentian were placed in 500 ml polypropylene cups together with dishes of water. These were coated at their tops with Saran wrap to seal them and were allowed to stand at 37° C. for 7 days, whereupon the untreated gentian discolored and turned brown and was observed to have a white mold, while the surface treated gentian maintained its original color and did not showed any mold.

In the above way, since the dry flower of the present invention is coated by a thin, transparent water resistant polymer film, it has sufficient water repellency without detracting from its original natural appearance and in particular is remarkably improved in its color stability and mold resistance under high humidity conditions.

INDUSTRIAL APPLICABILITY

The dry flower obtained by the present invention has the following features:

1) It is water repellant, and therefore, is resistant to absorption of moisture even under humid conditions.
2) Discoloring and molding due to adherence of moisture can be suppressed.
3) The dry flower will not change in the color or shape of its flower, leaves, or stem even under severe conditions.
4) The coating is extremely thin, so the effects of the above 1) to 3) can be obtained, while maintaining the original natural appearance of the dry flower.

We claim:

1. A dry flower coated on its surface with at least one transparent, water-resistant polymer film selected from the group consisting of (a) silicone polymers, (b) polymers obtained from photopolymerizable monomers, (c) polymers obtained from silane coupling agents, and (d) copolymers of photopolymerizable monomers and silane coupling agents, wherein said polymer coated onto the flower's surface in vapor form and in the absence of an organic solvent.

2. A dry flower as claimed in claim 1, wherein said polymer film is a silicone polymer film obtained by bringing at least one silicone compound of the formula (I):

$$(R^1HSiO)_a(R^2R^3SiO)_b(R^4R^5R^6SiO_{1/2})_c \qquad (I)$$

wherein $R^1$, $R^2$, and $R^3$ independently represent a hydrogen atom or a $C_1$ to $C_{10}$ hydrocarbon group which may be substituted with at least one halogen atom provided that $R^1$, $R^2$ and $R^6$ are not simultaneously hydrogen atoms; $R^4$, $R^5$, and $R^6$ independently represent a hydrogen atom or a $C_1$ to $C_{10}$ hydrocarbon group which may be substituted with at least one halogen atom, a is 0 or an integer of 1 or more, b is 0 or an integer of 1 or more, and c is 0 or 2, the sum of a and b being an integer of 3 or more when c is 0, into contact with a dry flower in the form of a vapor and polymerizing the silicone compound on the surface of the dry flower.

3. A dry flower as claimed in claim 1 wherein said polymer film comprises a copolymer with a silicone compound having a hydrosilyl bond (Si—H).

4. A dry flower as claimed in claim 1, wherein a polymerized film of a silicone compound having hydrosilyl bonds (Si—H), which are present inside and outside of the polymer film.

5. A process for producing a dry flower comprising bringing at least one silicone compound, in the form of a vapor and in the absence of an organic solvent, having the formula (I):

$$(R^1HSiO)_a(R^2R^3SiO)_b(R^4R^5R^6SiO_{1/2})_c \qquad (I)$$

wherein $R^1$, $R^2$, and $R^3$ independently represent a hydrogen atom or a $C_1$ to $C_{10}$ hydrocarbon group which may be substituted with at least one halogen atom provided that $R^1$, $R^2$, and $R^3$ are not simultaneously hydrogen atoms; $R^4$, $R^5$, and $R^6$ independently represent a hydrogen atom or a $C_1$ to $C_{10}$ hydrocarbon group which may be substituted with at least one halogen atom, a is 0 or an integer of 1 or more, b is 0 or an integer of 1 or more, and c is 0 or 2, the sum of a and b being an integer of 3 or more when c is 0, into contact with a flower and polymerizing the silicone compound on the surface of the dry flower so as to carry the film of the silicone polymer on the surface of the dry flower.

6. A process for producing a dry flower comprising bringing at least one member selected from the group consisting of (i) a photopolymerization initiator and photopolymerizable monomer and (ii) a silane coupling agent, in a vapor phase state and in the absence of an organic solvent, into contact with a surface of a dry flower and causing polymerization on the surface of the dry flower so as to coat the surface of the dry flower with a polymer film.

7. A process for producing a dry flower as claimed in claim 6, wherein, simultaneously with the step of forming the polymer film or as a step before or a step after said step, a silicone compound, in a vapor phase state, having a hydrosilyl bond (Si—H) is brought into contact with the surface of the dry flower and polymerized on the surface of the dry flower.

* * * * *